United States Patent [19]

Ohashi et al.

[11] Patent Number: 4,544,635
[45] Date of Patent: Oct. 1, 1985

[54] PREPARATION OF OPTICALLY ACTIVE CIS-1,3-DIBENZYL-HEXAHYDRO-1H-FURO[3,4-d]IMIDAZOLE-2,4-DIONE AND ITS INTERMEDIATES

[75] Inventors: Naohito Ohashi, Hyogo; Kozo Shimago, Osaka; Takaharu Ikeda, Osaka; Kikuo Ishizumi, Osaka, all of Japan

[73] Assignee: Sumitomo Chemical Co., Ltd., Osaka, Japan

[21] Appl. No.: 579,602

[22] Filed: Feb. 13, 1984

Related U.S. Application Data

[62] Division of Ser. No. 460,797, Jan. 25, 1983, Pat. No. 4,496,739.

[30] Foreign Application Priority Data

Jan. 27, 1982 [JP] Japan ................................. 57-12132
Apr. 28, 1982 [JP] Japan ................................. 57-71834
Apr. 28, 1982 [JP] Japan ................................. 57-71837
Apr. 30, 1982 [JP] Japan ................................. 57-73938

[51] Int. Cl.[4] ............... C12P 17/10; C07D 491/048
[52] U.S. Cl. .................................. 435/121; 548/303; 548/321
[58] Field of Search ................. 435/121; 548/303, 321

[56] References Cited

U.S. PATENT DOCUMENTS 3,700,659 10/1972 Gerecke et al. ............. 548/303 X
4,496,739 1/1985 Ohashi et al. ............... 548/321

FOREIGN PATENT DOCUMENTS 57-198098 12/1982 Japan ........................... 548/303

OTHER PUBLICATIONS

House, H., *Modern Synthetic Reactions*, 2nd Edition, Benjamin/Cummings, Menlo Park, CA, 1972, pp. 71, 77 and 78.

Iriuchijima, S., et al., *Agric. Biol. Chem.*, 46(7), 1907–1910 (1982).
Iriuchijima, S., et al., Speech Given at Meeting of Association of Agricultural Chemistry of Japan, Apr. 1–4, 1982, Tokyo, Japan.

*Primary Examiner*—Richard A. Schwartz
*Attorney, Agent, or Firm*—Birch, Stewart, Kolasch & Birch

[57] ABSTRACT

A process for preparing an optically active cis-1,3-dibenzylhexahydro-1H-furo[3,4-d]imidazole-2,4-dione of the formula:

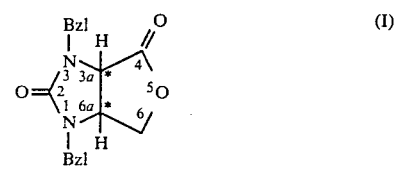

wherein an asterisk (*) indicates an asymmetric carbon, Bzl represents a benzyl group and the 3a- and 6a-positions take the cis-configuration, which comprises reducing selectively an optically active cis-imidazolidinedicarboxylic acid monoester of the formula:

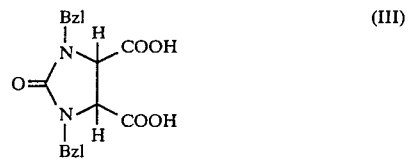

wherein R is a $C_1$–$C_6$ alkyl group and Bzl is as defined above with a reducing agent at either one of the carboxyl group and the alkoxycarbonyl group in the said monoester, followed by cyclization.

17 Claims, No Drawings

PREPARATION OF OPTICALLY ACTIVE CIS-1,3-DIBENZYL-HEXAHYDRO-1H-FURO[3,4-d]IMIDAZOLE-2,4-DIONE AND ITS INTERMEDIATES

This application is a divisional of application Ser. No. 460,797, filed on Jan. 25, 1983, now U.S. Pat. No. 4,496,739.

This invention relates to preparation of optically active cis-1,3-dibenzyl-hexahydro-1H-furo[3,4-d]imidazole-2,4-dione and its intermediates.

More particularly, it relates to preparation of an optically active cis-1,3-dibenzyl-hexahydro-1H-furo[3,4-d]-imidazole-2,4-dione of the formula:

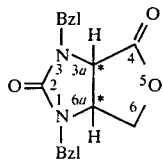

wherein an asterisk (*) indicates an asymmetric carbon, Bzl represents a benzyl group and the 3a- and 6a-positions take the cis-configuration (hereinafter referred to as "lactone") through an optically active cis-imidazolidinedicarboxylic acid monoester of the formula:

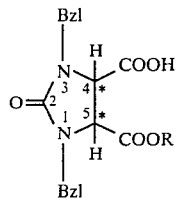

wherein an asterisk (*) indicates an asymmetric carbon, R is a $C_1$–$C_6$ alkyl group, Bzl represents a benzyl group and the 4- and 5-positions take the 4S,5R- or 4R,5S-configuration (hereinafter referred to as "half-ester").

Examples of the said "$C_1$–$C_6$ alkyl" group are methyl, ethyl, n-propyl, n-butyl, t-butyl, n-pentyl, n-hexyl, etc.

For preparation of the optically active lactone (I), there are known the process as disclosed in U.S. Pat. No. 3,700,659 (Process (A)) and the process as disclosed in U.S. Pat. No. 3,876,656 (Process (B)).

In the process (A), (±)-cis-1,3-dibenzyl-5-(3'-cholesteryloxycarbonyl)-2-oxoimidazolidine-4-carboxylic acid is subjected to optical resolution in the form of triethylamine salt and the resulting optically active cholesteryl half-ester is reduced with lithium borohydride to obtain the optically active lactone (I). Alternatively, (±)-cis-1,3-dibenzyl-5-cyclohexyloxycarbonyl-2-oxoimidazolidine-4-carboxylic acid is subjected to optical resolution in the form of ephedrine salt and the resultant optically active cyclohexyl half-ester is reduced with lithium borohydride to give the optically active lactone (I). However, these procedures are disadvantageous in requiring the use of an expensive substance such as ephedrine or cholesterol and giving the objective optically active lactone (I) only in a low total yield. In addition, only one of the optical isomers of the cholesteryl half-ester or the cyclohexyl half-ester obtained in the optical resolution can participate in the reduction with lithium borohydride to give the optically active lactone (I), while the other optical isomer is returned to a certain initial step for the use as the starting material (cf. column 4, lines 1 to 6). Thus, the two optical isomers resulting from the optical resolution can not be simultaneously subjected to reduction for production of the optically active lactone (I).

The process (B) comprises subjecting the cis-1,3-dibenzyl-hexahydropyrrolo[3,4-d]imidazole-2,4,6-trione derivative, obtained by dehydration between bis-1,3-dibenzyl-2-oxoimidazolidine-4,5-dicarboxylic acid and an optically active organic primary amine, to asymmetric reduction with sodium borohydride and hydrolyzing the resulting product to give the optically active lactone (I). This process is also disadvantageous in requiring the use of an expensive amine and affording only an insufficient asymmetric yield.

As a result of an extensive study, it has now been found that the optically active lactone (I) can be produced in an excellent yield from a cis-imidazolidine-dicarboxylic acid diester of the formula:

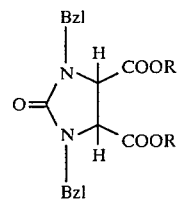

wherein R is as defined above and Bzl means a benzyl group (hereinafter referred to as "diester") through the optically active half-ester (III).

According to the present invention, there is provided an industrially advantageous process for preparing the optically active lactone (I) which comprises converting the diester (II) into the optically active half-ester (III) and converting the latter into the optically active lactone (I).

The conversion of the diester (II) into the optically active half-ester (III) can be accomplished by treatment of the diester (II) with an enzymatic material having a capability of hydrolyzing the ester bond in the diester (II). As the enzymatic material having a hydrolytic property, there are known numerous and various ones. Quite surprisingly, however, only certain specific enzymatic materials are effective in cleavage of the ester bond in the diester (II) and can be used in the above conversion. For instance, hydrolytic enzymes such as trypsin originating from bovine pancreas, α-chymotrypsin originating from bovine pancreas, lypase originating from Candida clindracea and lypase originating from pig pancreas as well as microorganisms having hydrolytic ability such as *Gliocladium roseum, Helminthosporium* sp. and *Zygorhynchus moelleri* can not achieve said cleavage, while esterase originating from pig liver and esterase originating from any microorganism belonging to Genus Chromobacterium such as *Chromobacterium chocolatum* can accomplish said cleavage. Thus, the enzymatic material usable in this invention is any one chosen from esterase originating from pig liver and esterase originating from any microorganism belonging to Genus Chromobacterium. Such esterase is not necessarily required to be isolated or pure. For instance, an esterase-producing strain of a microorganism belonging to Genus Chromobacterium may be used as such instead of the esterase separated from such strain or its cultivation product. The hydrolysis of the diester (II) with said enzymatic material proceeds almost quantitatively to give the optically active half-ester (III). In addition, it can proceed stereospecifically so that the produced optically active half-ester (III) takes the 4S,5R-configuration. Still, the use of said specific enzymatic material for successful hydrolysis of the diester (II) to the optically active half-ester (III) has never been known and falls within the scope of this invention.

The hydrolysis of the diester (II) with the enzymatic material will be hereinafter explained more in detail.

When the enzymatic material is pig liver esterase, the hydrolysis may be carried out, for instance, by suspending or dissolving the diester (II) in an aqueous medium having a pH of 2 to 10, preferably of 5 to 9, adding pig liver esterase thereto and stirring the resultant medium at a temperature of 0° to 60° C., preferably of 10° to 40° C., for a period of 1 hour to several days. The pig liver esterase is known [Biochem.Biophys.Res.Comm., 23, 23 (1966)] and commercially available. The amount of the enzyme to be used depends upon the degree of purification. When commercially available pig liver esterase (Sigma Chem. Co.; 160 units/mg protein; one unit will hydrolyze 1.0 mole of ethyl butyrate to butyric acid and ethanol per minute) is employed, its amount may be from 0.001 to 0.1 part by weight to one part by weight of the diester (II). The concentration of the diester (II) as the substrate may be usually from 0.1 to 10% by weight.

When the enzymatic material is an esterase-producing Chromobacterium microorganism, its strain is first cultured in a conventional aqueous nutrient medium. From the very beginning or at a certain stage of the cultivation, the diester (II) may be added to the medium, whereby the hydrolysis proceeds with the cultivation. Insofar as the growth of the strain is assured, any limitation is not present on the temperature, but usually a temperature of 25° to 37° C. is favored for the cultivation. In such case, the cultivation period may be from a half day to 7 days, and the concentration of the diester (II) as the substrate can be made from 0.1 to 10% by weight.

Alternatively, the cultivated medium may be subjected to appropriate separation treatment such as centrifugation so as to use the collected bacterial cells for the hydrolysis. When desired, the bacterial cells may be subjected to ultrasonic treatment or lysozyme treatment to liberate the enzyme substance, which is collected by an appropriate separation procedure such as centrifugation, fraction with ammonium sulfate or dialysis and then used for the hydrolysis. In these cases, the diester (II) may be suspended or dissolved in an aqueous medium having a pH of 5 to 9, the bacterial cells or the enzymatic substance is added therto in an amount of 0.001 to 0.1 parts by weight to one part by weight of the diester (II), and the resulant suspension or solution is stirred at a temperature of 10° to 40° C., usually for a period of 1 hour to several days.

The aqueous medium as hereinabove mentioned may contain a mineral acid (e.g. sulfuric acid, hydrochloric acid, phosphoric acid), an organic acid (e.g. acetic acid, citric acid), an inorganic base (e.g. sodium hydroxide, potassium hydroxide, sodium carbonate), an organic base (e.g. triethylamine, pyridine), a salt (e.g. sodium acetate, sodium chloride) or the like. As the aqueous medium, there may be used a buffer containing potassium dihydrogen phosphate/sodium hydroxide, potassium dihydrogen phosphate/sodium dihydrogen phosphate, potassium hydrogen phthalate/hydrochloric acid, glycine/sodium chloride/sodium hydroxide or the like. When desired, the aqueous medium may further contain any organic solvent such as an alcohol (e.g. methanol, ethanol, n-propanol, isopropanol, n-butanol, t-butanol), an ether (e.g. diethyl ether, tetrahydrofuran, dioxane), an aromatic hydrocarbon (e.g. benzene, toluene), a ketone (e.g. acetone, methylethylketone, diethylketone), an amine (e.g. triethylamine, pyridine) or a polar solvent (e.g. dimethylformamide, dimethylsulfoxide) as well as a surfactant such as sorbitan monopalmitate or sorbitan monolaurate.

The optically active half-ester (III) may be prepared through a different route. Namely, cis-1,3-dibenzyl-hexahydro-1H-furo[3,4-d]imidazole-2,4,6-trione and a lower alkanol are reacted to give the half-ester (III) in a racemic form. Then, the racemic half-ester (III) is subjected to optical resolution using optically active ephedrine or optically active 2-amino-1,1-diphenylpropanol to give the corresponding optically active half-ester (III) in the 4S,5R- or 4R,5S-configuration.

In the above optical resolution, one mole of the racemic half-ester (III) is usually treated with 0.7 to 1.1 mole of an optically active amine such as optically active ephedrine or optically active 2-amino-1,1-diphenylpropanol in an inert solvent such as an alcoholic solvent (e.g. ethanol, isopropanol) or acetonitrile to make the diastereomer salt, which is separated into the (4S,5R)-half-ester/optically active amine salt and the (4R,5S)-half-ester/optically active amine salt by the utilization of the difference in solubility. Each of the resulting salts is treated with a mineral acid (e.g. sulfuric acid, hydrochloric acid) to give the optically active half-ester (III) having the 4S,5R- or 4R,5S-configuration.

The conversion of the optically active half-ester (III) into the optically active lactone (I) can be achieved by selective reduction of either one of the carboxyl group and the alkoxycarbonyl group in the former, followed by cyclization. Depending upon whether the reduction proceeds at the carboxyl group or at the alkoxycarbonyl group, there is obtained the optically active lactone (I) having a different configuration. When the reduction proceeds at the alkoxycarbonyl group in the half-ester (III) having the 4S,5R-configuration, the produced lactone (I) takes the 3aS,6aR-configuration. When the reduction proceeds at the carboxyl group in the said half-ester (III), the produced lactone (I) takes the 3aR,6aS-configuration. On the other hand, the reduction of the carboxyl group in the half-ester (III) having the 4R,5S-configuration gives the lactone (I) having the 3aS,6aR-configuration, while the reduction of the alkoxycarbonyl group in the said half-ester (III) affords the lactone (I) having the 3aR,6aS-configuration. The above relationships are shown in the following Scheme 1:

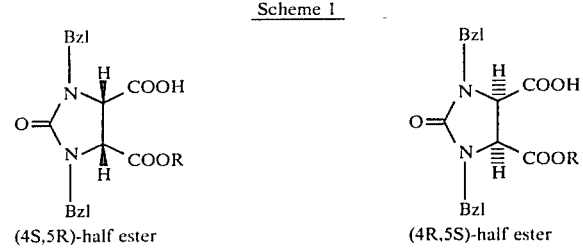

Scheme 1

(4S,5R)-half ester    (4R,5S)-half ester

-continued
Scheme 1

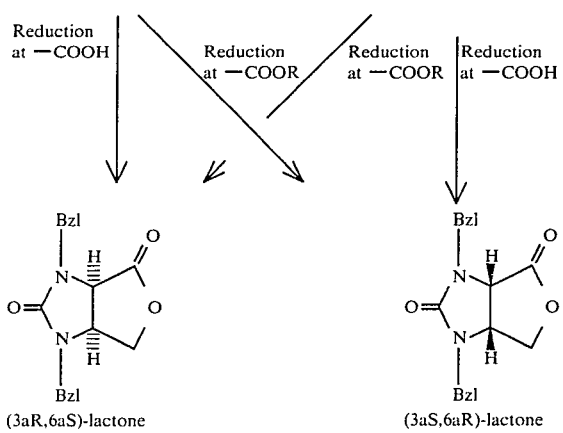

(3aR,6aS)-lactone            (3aS,6aR)-lactone wherein R is as defined above and Bzl represents a benzyl group.

For the selective reduction of the alkoxycarbonyl group in the optically active half-ester (III), there may be used a reducing agent such as sodium borohydride, lithium borohydride, calcium borohydride, diisobutyl aluminum hydride (DIBAL-H) or diethyl aluminum sodiohydride (OMH-1). The reduction is normally carried out in an inert solvent such as an ether (e.g. diethyl ether, tetrahydrofuran, dioxane, ethylene glycol dimethyl ether) or an aromatic or aliphatic hydrocarbon (e.g. toluene, hexane). In case of the reducing agent being a boron-containing reagent, an alcohol (e.g. ethanol, isopropanol) or its mixture with water may be also used as the medium. Usually, the reaction is effected at room temperature, although a wide range of temperature from cooling to refluxing may be adopted. When the reducing agent is an aluminum-containing reagent, the reaction temperature from $-70°$ to $-20°$ C. is favored.

Among various reducing agents as stated above, preferred is a boron-containing reagent. Sodium borohydride is particularly favorable, because it is available at a low cost, can be handled with high safety and may be used under a mild condition to attain a good yield. In this connection, it should be noted that sodium borohydride is generally considered not to reduce an ester group such as alkoxycarbonyl [Fieser et al.: "Reagents for Organic Synthesis", John Wiley & Sons, Inc., New York, 1969, pages 1050 to 1051] and yet can achieve the selective reduction of the alkoxycarbonyl group in the optically active half-ester (III). It should be also noted that while the selective reduction with sodium borohydride in a sole solvent system such as water, methanol, ethanol, isopropanol or tetrahydrofuran as conventionally adopted can not attain a sufficient yield, that in a certain mixed solvent system, i.e. a mixture of an alcoholic solvent (e.g. ethanol, isopropanol) and an aprotic solvent (e.g. tetrahydrofuran, toluene, benzene, dichloromethane, chloroform, 1,2-dichloroethane, dioxane), attains a satisfactory yield. In this case, the volume proportion of the alcoholic solvent and the aprotic solvent may be 0.5-10:1. Further, the amount of sodium borohydride may be from 0.8 to 5 mol, particularly from 1 to 2 mol, to 1 mol of the optically active half-ester (III). The reaction temperature is usually from $-10°$ to $50°$ C., preferably from $0°$ to $30°$ C.

For the selective reduction of the carboxyl group in the optically active half-ester (III), there may be used a reducing agent such as diborane. When desired, the carboxyl group may be once converted into a reactive form such as an active ester, a mixed acid anhydride or an acid halide by reacting the former with an appropriate reagent such as N-hydroxysuccinimide, p-nitrophenol, isobutyl chloroformate, ethyl chloroformat or thionyl chloride, followed by reaction with a reducing agent such as sodium borohydride.

When the reducing agent is diborane, it may be employed in an amount of 0.5 to 3 mol, preferably of 0.5 to 1 mol, to one mol of the optically active half-ester (III). The reduction is normally carried out in an inert solvent such as a halogenated alkane (e.g. dichloromethane, 1,2-dichloroethane), an ether (e.g. tetrahydrofuran, dioxane) or an aromatic hydrocarbon (e.g. benzene, toluene) at a temperature of $0°$ to $40°$ C. Diborane may be any commercially available one or prepared from sodium borohydride or lithium borohydride and a Lewis acid (e.g. boron trifluoride) according to a conventional procedure. From the industrial viewpoint, the reduction is preferably carried out by reacting sodium borohydride with a Lewis acid (e.g. boron trifluoride) in an inert solvent (e.g. tetrahydrofuran, dioxane) at a temperature of $-10°$ to $40°$ C. and adding the optically active half-ester (III) to the resultant diborane solution, or by adding a Lewis acid (e.g. boron trifluoride) to a solution comprising sodium borohydride and the optically active half-ester (III). In these cases, sodium borohydride may be used in an amount of 0.75 to 4.5 mol, especially of 0.75 to 1.5 mol, to one mol of the optically active half-ester (III), and the Lewis acid may be employed in an amount of 1 to 10 mol, particularly of 1 to 4 mol, to one mol of the said half-ester (III).

The reduction with the previous conversion of the carboxyl group into the form of active ester, mixed acid anhydride or acid halide may be carried out in a per se conventional procedure [Chem.Pharm.Bull.Japan, 16, 492 (1968)].

After the reduction is completed, the reaction mixture is made neutral or acidic, followed by extraction with an approriate solvent such as dichloromethane, 1,2-dichloroethane, toluene or ethyl acetate. At that time, the cyclization proceeds spontaneously to give the optically active lactone (I). In order to attain a better yield, it is preferred to make the said reaction mixture acidic rather than neutral.

The thus prepared optically active lactone (I) is known to be useful as the starting material in the production of medicines. For instance, the optically active lactone (I) having the 3aS,6aR-configuration is an important intermediate in the synthesis of naturally occurring biotin [British Pat. Nos. 1,320,798 and 1,320,799]. Further, for instance, the optically active lactone (I) having the 3aR,6aS-configuration is an important intermediate in the synthesis of trimethaphan having a blood pressure lowering activity [J.Pharmacol.Exp.Therap., 97, 48 (1949)].

The diester (II) and the racemic half-ester (III) used as the starting materials may be prepared according to the following scheme 2:

Scheme 2

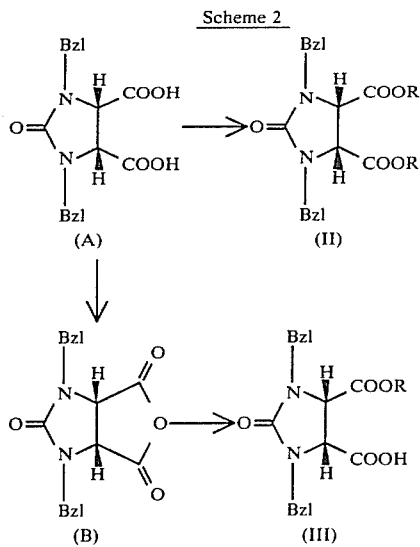

wherein R is as defined above.

Namely, the diester (II) may be produced by reacting the compound (A) with a lower alkanol in the presence of an acid catalyst (e.g. sulfuric acid, hydrochloric acid, p-toluenesulfonic acid, boron trifluoride). The racemic half-ester (III) may be produced by treating the compound (A) with thionyl chloride or acetic anhydride to give the acid anhydride (B), followed by reaction with a lower alkanol.

Practical and presently preferred embodiments of the invention are illustratively shown in the following examples.

EXAMPLE 1

(1) To a suspension of dimethyl cis-1,3-dibenzyl-2-oxoimidazolidine-4,5-dicarboxylate (500 mg) in 0.1M phosphate buffer (pH 8.0, 50 ml) was added Pig Liver Esterase (manufactured by Sigma Lab., 1600 units, 10 mg). The mixture was stirred at room temperature for 30 hours. Chloroform (150 ml) was added to the mixture. Then, the mixture was adjusted to pH 2 with diluted sulfuric acid. The chloroform layer was separated from the aqueous layer, washed with water, dried over anhydrous magnesium sulfate and concentrated to give (4S,5R)-1,3-dibenzyl-5-methoxycarbonyl-2-oxoimidazolidine-4-carboxylic acid (435 mg). M.P., 141°–146° C. $[\alpha]_D^{20} = +2.0°$ (c=1, CHCl$_3$). $[\alpha]_{365}^{20} = -21.6°$ (c=1, DMF).

The above half-ester was recrystallized twice from benzene to give purified product. M.P., 149°–150° C. $[\alpha]_{365}^{20} = -27.6°$ (c=1, DMF).

(2) To a mixture of lithium borohydride (43 mg) and tetrahydrofuran (3 ml) was added dropwise a solution of unpurified (4S,5R)-1,3-dibenzyl-5-methoxycarbonyl-2-oxoimidazolidine-4-carboxylic acid (240 mg) obtained in (1) in tetrahydrofuran (4 ml) at room temperature. The reaction mixture was refluxed for 2 hours and tetrahydrofuran was removed by distillation. To the residue was added methanol (4 ml) gradually under cooling and then conc. hydrochloric acid (0.5 g). The mixture was refluxed for 1 hour and concentrated under reduced pressure. The residue was purified by chromatography on silica gel column to give (3aS,6aR)-1,3-dibenzylhexahydro-1H-furo[3,4-d]imidazole-2,4-dione (165 mg). M.P., 110°–115° C. $[\alpha]_D^{20} = +47.9°$ (c=1, CHCl$_3$).

EXAMPLE 2

(1) To a suspension of dimethyl cis-1,3-dibenzyl-2-dibenzyl-2-oxoimidazolidine-4,5-dicarboxylate (500 mg) in a mixture of 0.1M phosphate buffer (pH 8.0, 45 ml) and methanol (5 ml) was added Pig Liver Esterase (manufactured by Sigma Lab., 1600 units, 10 mg). The mixture was treated in a manner similar to that in Example 1 (1) to give (4S,5R)-1,3-dibenzyl-5-methoxycarbonyl-2-oxoimidazolidine-4-carboxylic acid (360 mg). M.P., 142°–146° C. $[\alpha]_D^{20} = +2.2°$ (c=1, CHCl$_3$).

(2) The half-ester (240 mg) obtained in (1) was reduced and cyclized in a manner similar to that in Example 1 (2) to give (3aS,6aR)-1,3-dibenzylhexahydro-1H-furo[3,4-d]imidazole-2,4-dione (163 mg). M.P., 108°–110° C. $[\alpha]_D^{20} = +53.7°$ (c=1, CHCl$_3$).

EXAMPLE 3

(1) To a suspension of dimethyl cis-1,3-dibenzyl-2-oxoimidazolidine-4,5-dicarboxylate (10.0 g) in a mixture of 0.1M phosphate buffer (pH 8.0, 900 ml) and methanol (100 ml) was added Pig Liver Esterase (manufactured by Sigma Lab., 32000 units, 200 mg). The mixture was stirred at 30° C. for 42 hours while the pH was adjusted to around 8.0 with 1N aqueous sodium hydroxide solution. Chloroform (500 ml) was added to the mixture. Then, the mixture was adjusted to pH 2 with diluted sulfuric acid. The aqueous and chloroform layers were separated. The chloroform layer was washed with water, dried over anhydrous magnesium sulfate and concentrated to give (4S,5R)-1,3-dibenzyl-5-methoxycarbonyl-2-oxoimidazolidine-4-carboxylic acid (8.80 g). M.P., 145°–147° C. $[\alpha]_{365}^{20} = -25.3°$ (c=1, DMF).

The above-half ester was recrystallized twice from benzene (400 ml) to give purified product (7.07 g). M.P., 149°–150° C. $[\alpha]_{365}^{20} = -27.7°$ (c=1, DMF).

(2) To a mixture of sodium borohydride (640 mg) and isopropanol (70 ml) was added dropwise a solution of the half-ester (2.40 g) obtained in (1) in tetrahydrofuran (30 ml) at room temperature. The mixture was stirred at 60°–70° C. for 7 hours, cooled and concentrated under reduced pressure after adding conc. hydrochloric acid (510 g). Water (500 ml) was added to the residue, which was then extracted twice with chloroform (200 ml). The chloroform layer was washed with water, dried over anhydrous magnesium sulfate and concentrated under reduced pressure to give residue (2.07 g), which was recrystallized from aqueous isopropanol to yield (3aS,6aR)-1,3-dibenzylhexahydro-1H-furo[3,4-d]imidazole-3,4-dione (1.83 g).

EXAMPLE 4

(1) A solution of glucose (1.0 g), yeast extract (manufactured by Kyokuto Pharmaceutical Co., 0.5 g), peptone (manufactured by Mikuni Chemical, 1.0 g) and dipotassium hydrogen phosphate (0.5 g) in distilled water (100 ml) was adjusted to pH 7.0 with diluted hydrochloric acid. The obtained liquid medium was sterilized by steam at 120° C. for 20 minutes, inoculated with *Chromobacterium chocolatum* IFO-3758 and cultured with shaking at 26° C. for 48 hours. Then, dimethyl cis-1,3-dibenzyl-2-oxoimidazolidine-4,5-dicarboxylate (400 mg) was added to the medium, which was further shaken at 26° C. for 72 hours. After adding ethyl acetate (100 ml), the medium was acidified with diluted hydrochloric acid and filtered through a layer of celite.

The aqueous and organic layers in the filtrate were separated. The organic layer was washed with water, dried over anhydrous magnesium sulfate and concentrated under reduced pressure. The residue was dissolved in 5% aqueous sodium hydrogen carbonate (20 ml). The solution was washed with ether (20 ml) and adjusted to pH 2 with diluted sulfuric acid to precipitate white crystals, which were filtered, washed with water and dried to yield (4S,5R)-1,3-dibenzyl-5-methoxycarbonyl-2-oxoimidazolidine-4-carboxylic acid (340 mg). M.P., 149°-151° C. $[\alpha]_{365}^{20} = -28.0°$ (c=1, DMF).

(2) The half-ester (240 mg) obtained in (1) was reduced and cyclized in a manner similar to that in Example 1 (2) to give (3aS,6aR)-1,3-dibenzylhexahydro-1H-furo-[3,4-d]imidazole-2,4-dione (183 mg). M.P., 117°-118° C. $[\alpha]_D^{20} = +62.5°$ (c=1, CHCl$_3$).

EXAMPLE 5

(1) A solution of glucose (3.0 g), yeast extract (manufactured by Kyokuto Pharmaceutical Co., 1.5 g), peptone (manufactured by Mikuni Chemical, 3.0 g) and dipotassium hydrogen phosphate (1.5 g) in distilled water (300 ml) was adjusted to pH 7.0 with diluted hydrochloric acid. The obtained liquid medium was sterilized by steam at 120° C. for 20 minutes, inoculated with *Chromobacterium chocolatum* IFO-3758 and cultured with shaking at 26° C. for 72 hours. The medium was centrifuged at 5000 rpm for 25 minutes under cooling. The fungus bodies were washed thrice with 0.85% aqueous sodium chloride (100 ml) and collected by centrifugation. To the fungus bodies were added 0.1M phosphate buffer (pH 7.0, 50 ml) and dimethyl cis-1,3-dibenzyl-2-oxoimidazolidine-4,5-dicarboxylate (1.50 g). The mixture was stirred at room temperature for 70 hours while the pH was adjusted to around 7 with 1N sodium hydroxide, filtered through a layer of celite and adjusted to pH 2 with diluted sulfuric acid to precipitate white crystals, which were filtered, washed with water and dried to give (4S,5R)-1,3-dibenzyl-5-methoxycarbonyl-2-oxoimidazolidine-4-carboxylic acid (1.40 g). M.P., 146°-148° C. $[\alpha]_{365}^{20} = -26.0°$ (c=1, DMF).

(2) The half-ester (1.0 g) obtained in (1) was reduced and cyclized in a manner similar to that in Example 1 (2) to give (3aS,6aR)-1,3-dibenzylhexahydro-1H-furo-[3,4-d]imidazole-2,4-dione (0.72 g). M.P., 115°-117° C. $[\alpha]_D^{20} = +60.1°$ (c=1, CHCl$_3$).

EXAMPLE 6

(1) A suspension of diethyl cis-1,3-dibenzyl-2-oxoimidazolidine-4,5-dicarboxylate (500 mg) in 0.1M phosphate buffer (pH 8.0, 50 ml) was treated with Pig Liver Esterase (manufactured by Sigma Lab., 1600 units, 10 mg) in a manner similar to that in Example 1 (1) to give (4S,5R)-1,3-dibenzyl-5-ethoxycarbonyl-2-oxoimidazolidine-4-carboxylic acid (400 mg). M.P., 108°-112° C. $[\alpha]_D^{20} = +4.4°$ (c=1, CHCl$_3$).

(2) The half-ester (248 mg) obtained in (1) was reduced and cyclized in a manner similar to that in Example 1 (2) to give (3aS,6aR)-1,3-dibenzylhexahydro-1H-furo-[3,4-d]imidazole-2,4-dione (159 mg). M.P., 108°-110° C. $[\alpha]_D^{20} = +46.3°$ (c=1, CHCl$_3$).

(3) A mixture of cis-1,3-dibenzyl-2-oxoimidazolidine-4,5-dicarboxylic acid (35.4 g), benzene (500 ml), 99.5% ethanol (45 ml) and conc. sulfuric acid (5.0 g) was refluxed for 10 hours, cooled, washed successively with water, 5% aqueous sodium hydroxide and water, and then concentrated under reduced pressure. The residue was recrystallized from 95% ethanol to give diethyl cis-1,3-dibenzyl-2-oxoimidazolidine-4,5-dicarboxylate (32.1 g). M.P., 74°-76° C.

EXAMPLE 7

(1) A suspension of di-n-propyl cis-1,3-dibenzyl-2-oxoimidazolidine-4,5-dicarboxylate (200 mg) in 0.1M phosphate buffer (pH 8.0, 20 ml) was treated with Pig Liver Esterase (manufactured by Sigma Lab., 640 units, 4 mg) in a manner similar to that in Example 1 (1) to give (4S,5R)-1,3-dibenzyl-5-n-propoxycarbonyl-2-oxoimidazolidine-4-carboxylic acid (164 mg). M.P., 75°-90° C. $[\alpha]_D^{20} = +2.1°$ (c=1, CHCl$_3$).

(2) The half-ester (145 mg) obtained in (1) was reduced and cyclized in a manner similar to that in Example 1 (2) to give (3aS,6aR)-1,3-dibenzylhexahydro-1H-furo-[3,4-d]imidazole-2,4-dione (100 mg). M.P., 107°-110° C. $[\alpha]_D^{20} = +38.2°$ (c=1, CHCl$_3$).

(3) A mixture of cis-1,3-dibenzyl-2-oxoimidazolidine-4,5-dicarboxylic acid (35.4 g), benzene (500 ml), n-propanol (45 ml) and conc. sulfuric acid (5.0 g) was refluxed for 14 hours, cooled, washed successively with water, 5% aqueous sodium hydroxide and water, and then concentrated under reduced pressure to give oily product of di-n-propyl cis-1,3-dibenzyl-2-oxoimidazolidine-4,5-dicarboxylate (42.3 g). IR (neat, cm$^{-1}$): 2970, 1750, 1710, 1445, 1420, 1360, 1210, 1055, 750, 700.

EXAMPLE 8

(1) A suspension of di-n-butyl cis-1,3-dibenzyl-2-oxoimidazolidine-4,5-dicarboxylate (500 mg) in 0.1M phosphate buffer (pH 8.0, 45 ml) was treated with Pig Liver Esterase (manufactured by Sigma Lab., 1600 units, 10 mg) in a manner similar to that in Example 1 (1) to give (4S,5R)-1,3-dibenzyl-5-n-butyloxycarbonyl-2-oxoimidazolidine-4-carboxylic acid as an oily product. $[\alpha]_D^{20} = +4.1°$ (c=1.55, CHCl$_3$).

(2) The half-ester (266 mg) obtained in (1) was reduced and cyclized in a manner similar to that in Example 1 (2) to give (3aS,6aR)-1,3-dibenzylhexahydro-1H-furo[3,4-d]imidazole-2,4-dione (160 mg). M.P., 105°-107° C. $[\alpha]_D^{20} = +33.7°$ (c=1, CHCl$_3$).

(3) A mixture of cis-1,3-dibenzyl-2-oxoimidazolidine-4,5-dicarboxylic acid (35.4 g), benzene (500 ml), n-butanol (45 ml) and conc. sulfuric acid (5.0 g) was refluxed for 16 hours, cooled, washed successively with water, 5% aqueous sodium hydroxide and water, and then concentrated under reduced pressure to give oily product of di-n-butyl cis-1,3-dibenzyl-2-oxoimidazolidine-4,5-dicarboxylate (39.5 g). IR (neat, cm$^{-1}$): 2950, 1750, 1710, 1445, 1420, 1350, 1200, 1060, 1020, 960, 745, 695.

EXAMPLE 9

(1) A mixture of cis-1,3-dibenzyl-2-oxoimidazolidine-4,5-dicarboxylic acid anhydride (68.0 g), toluene (800 ml) and methanol (12.4 g) was reacted at 80°-82° C. for 3 hours and cooled to room temperature. Crystals produced were filtered and dried under reduced pressure to yield racemic cis-1,3-dibenzyl-5-methoxycarbonyl-2-oxoimidazolidine-4-carboxylic acid (61.3 g). M.P., 130°-131° C.

The above half-ester was recrystallized from toluene to give purified product. M.P., 131°-132° C.

(2) A solution of racemic cis-1,3-dibenzyl-5-methoxycarbonyl-2-oxoimidazolidine-4-carboxylic acid (3.68 g) and S-2-amino-1,1-diphenylpropanol (2.27 g) in isopropanol (40 ml) was allowed to react at room temperature for 3 hours. Crystals produced were filtered to yield a salt of (4S,5R)-cis-1,3-dibenzyl-5-methoxycarbonyl-2-oxo-imidazolidine-4-carboxylic acid with S-2-amino-1,1-diphenylpropanol (2.16 g). M.P., 105°–127° C. $[\alpha]_D^{25} = +20.6°$ (c=1.0, CH$_3$OH).

The salt (2.00 g) was treated with 3% hydrochloric acid. The obtained mixture was extracted with ethyl acetate and post-treated to give (4S,5R)-cis-1,3-dibenzyl-5-methoxycarbonyl-2-oxoimidazolidine-4-carboxylic acid (1.11 g). M.P., 144°–146° C. $[\alpha]_{365}^{25} = -25.5°$ (c=1.0, DMF).

The mother liquor of the salt was concentrated under reduced pressure. The residue was treated with 3% hydrochloric acid. The obtained mixture was extracted with ethyl acetate. The extract was concentrated and the residue was recrystallized from benzene to give (4R,5S)-cis-1,3-dibenzyl-5-methoxycarbonyl-2-oxoimidazolidine-4-carboxylic acid (0.96 g). M.P., 149°–150° C. $[\alpha]_{365}^{25} = +27.1°$ (c=1.0, DMF).

EXAMPLE 10

(1) A mixture of cis-1,3-dibenzyl-2-oxoimidazolidine-4,5-dicarboxylic acid anhydride (70.0 g), 99.5% ethanol (16.6 g) and benzene (1000 ml) was heated under reflux for 2 hours. The reaction mixture (about 600 ml) was concentrated under ordinary pressure. The residue was stirred overnight with n-hexane (200 ml). Crystals produced were filtered and dried under reduced pressure to yield racemic cis-1,3-dibenzyl-5-ethoxycarbonyl-2-oxoimidazolidine-4-carboxylic acid (76.2 g), which were recrystallized from toluene. M.P. 110°–111° C.

(2) To a solution of racemic cis-1,3-dibenzyl-5-ethoxycarbonyl-2-oxoimidazolidine-4-carboxylic acid (764 mg) in 95% ethanol (4 ml) was added l-ephedrine (310 mg). After it had dissolved completely, the solution was allowed to stand overnight at 0°–5° C. Crystals produced were filtered to yield a salt of (4R,5S)-cis-1,3-dibenzyl-5-ethoxycarbonyl-2-oxoimidazolidine-4-carboxylic acid with l-ephedrine (339 mg). M.P., 163°–167° C. $[\alpha]_D^{20} = -11.6°$ (c=1, CH$_3$OH).

The salt (200 mg) was treated with 3% hydrochloric acid (20 ml). The obtained mixture was extracted with ethyl acetate and post-treated to give (4R,5S)-cis-1,3-dibenzyl-5-ethoxycarbonyl-2-oxoimidazolidine-4-carboxylic acid (138 mg). M.P., 133°–135° C. $[\alpha]_{365}^{20} = +21.6°$ (c=1.0, DMF).

(3) To a solution of racemic cis-1,3-dibenzyl-5-ethoxycarbonyl-2-oxoimidazolidine-4-carboxylic acid (19.1 g) in isopropanol (200 ml) was added S-2-amino-1,1-diphenylpropanol (11.4 g). After it had dissolved completely, the solution was allowed to stand overnight at room temperature. Crystals produced were filtered to yield a salt (21.1 g, mp. 135°–144° C.), which (20.0 g) was recrystallized from methanol (500 ml) to give a salt of (4S,5R)-cis-1,3-dibenzyl-5-ethoxycarbonyl-2-oxoimidazolidine-4-carboxylic acid with S-2-amino-1,1-diphenylpropanol (7.3 g). M.P., 150°–151° C. $[\alpha]_D^{20} = +20.9°$ (c=1.0, CH$_3$OH).

The salt (6.0 g) was treated with 3% hydrochloric acid (300 ml). The obtained mixture was extracted with ethyl acetate and post-treated to give (4S,5R)-cis-1,3-dibenzyl-5-ethoxycarbonyl-2-oxoimidazolidine-4-carboxylic acid (3.9 g). M.P., 133°–135° C. $[\alpha]_{365}^{25} = -20.7°$ (c=1, DMF).

The above compound was recrystallized from benzene to give purified product. M.P., 137.5°–138.5° C. $[\alpha]_{365}^{20} = -21.8°$ (c=1, DMF).

The mother liquor of optical resolution and methanolic mother liquor were combined and concentrated under reduced pressure. The residue was treated with 3% hydrochloric acid (800 ml). The resultant mixture was extracted with ethyl acetate. Ethyl acetate was removed from the extract under reduced pressure. The residue was dissolved in isopropanol (200 ml) and to this solution was added R-2-amino-1,1-diphenylpropanol (8.4 g). After it had dissolved completely, the solution was allowed to stand at room temperature for 6 hours. Produced crystals (15.0 g) were recrystallized from methanol (400 ml) to yield a salt of (4R,5S)-cis-1,3-dibenzyl-5-ethoxycarbonyl-2-oxoimidazolidine-4-carboxylic acid with R-2-amino-1,1-diphenylpropanol (8.2 g). M.P., 150°–151° C. $[\alpha]_D^{20} = -21.0°$ (c=1.0, CH$_3$OH).

The salt (6.0 g) was treated with 3% hydrochloric acid, extracted with ethyl acetate and post-treated to give (4R,5S)-cis-1,3-dibenzyl-5-ethoxycarbonyl-2-oxoimidazolidine-4-carboxylic acid (3.7 g). M.P., 134°–146° C. $[\alpha]_{365}^{20} = +21.0°$ (c=1, DMF).

EXAMPLE 11

(1) A mixture of cis-1,3-dibenzyl-2-oxoimidazolidine-4,5-dicarboxylic acid anhydride (16.8 g), benzene (230 ml) and isopropanol (5.50 g) was refluxed for 10 hours. A part (about 150 ml) of the reaction mixture was concentrated under reduced pressure. The residue was stirred with n-hexane (30 ml) at room temperature for 5 hours. Crystals produced were filtered and dried to yield racemic cis-1,3-dibenzyl-5-isopropoxycarbonyl-2-oxoimidazolidine-4-carboxylic acid (9.61 g). M.P., 108°–109° C.

The above racemic half-ester was recrystallized from toluene to give purified product. M.P., 111°–112° C.

(2) A solution of racemic cis-1,3-dibenzyl-5-isopropoxycarbonyl-2-oxoimidazolidine-4-carboxylic acid (3.96 g) and l-ephedrine (1.65 g) in isopropanol (10 ml) was allowed to stand overnight. Crystals produced were filtered to yield a salt of (4R,5S)-cis-1,3-dibenzyl-5-isopropoxycarbonyl-2-oxoimidazolidine-4-carboxylic acid with l-ephedrine (2.85 g). M.P., 165°–170° C. $[\alpha]_D^{25} = -11.9°$ (c=1.0, CH$_3$OH).

The salt (2.00 g) was treated with 3% hydrochloric acid. The obtained mixture was extracted with ethyl acetate and post-treated to give (4R,5S)-cis-1,3-dibenzyl-5-isopropoxycarbonyl-2-oxoimidazolidine-4-carboxylic acid (1.20 g). M.P. 112°–126° C. $[\alpha]_{365}^{25} = +11.1°$ (c=1.0, DMF).

The mother liquor of the salt was concentrated under reduced pressure. The residue was treated with 3% hydrochloric acid. The obtained mixture was extracted with ethyl acetate. The extract was concentrated uder reduced pressure. The residue was dissolved together with S-2-amino-1,1-diphenylpropanol (1.10 g) in isopropanol (10 ml). The solution was allowed to stand overnight at room temperature. Crystals produced were filtered to yield a salt of (4S,5R)-cis-1,3-dibenzyl-5-isopropoxycarbonyl-2-oxomidazolidine-4-carboxylic acid with S-2-amino-1,1-diphenylpropanol (1.83 g). M.P., 146°–150° C. $[\alpha]_D^{25} = +21.6°$ (c=1.0, CH$_3$OH).

The salt (1.80 g) was treated with 3% hydrochloric acid, extracted with ethyl acetate and post-treated to give (4S,5R)-cis-1,3-dibenzyl-5-isopropoxycarbonyl-2-oxoimidazolidine-4-carboxylic acid (1.00 g). M.P., 106°–123° C. $[\alpha]_{365}^{20} = -10.1°$ (c=1.0, DMF).

EXAMPLE 12

(1) A mixture of cis-1,3-dibenzyl-2-oxoimidazolidine-4-carboxylic acid anhydride (68.0 g), benzene (1000 ml)

and n-propanol (23.0 g) was refluxed for 3 hours. The reaction mixture was concentrated under reduced pressure. The residue was stirred with ether (150 ml) and n-hexane (45 ml) at room temperature for 15 hours. Crystals produced were filtered to yield racemic cis-1,3-dibenzyl-5-n-propoxycarbonyl-2-oxoimidazolidine-4-carboxylic acid (51.2 g). M.P., 82°–85° C.

The above crystals were recrystallized from a mixture of ether and n-hexane to give purified product. M.P., 84°–85° C.

(2) A solution of racemic cis-1,3-dibenzyl-5-n-propoxycarbonyl-2-oxoimidazolidine-4-carboxylic acid (3.96 g) and S-2-amino-1,1-diphenylpropanol (2.27 g) in isopropanol (10 ml) was allowed to stand overnight at room temperature. Crystals produced were filtered to yield a salt of (4R,5S)-cis-1,3-dibenzyl-5-n-propoxycarbonyl-2-oxoimidazolidine-4-carboxylic acid with S-2-amino-1,1-diphenylpropanol (0.48 g). M.P., 117°–125° C. $[\alpha]_D^{25} = +36.7°$ (c=0.1, CH$_3$OH).

The salt (0.40 g) was treated with 3% hydrochloric acid. The obtained mixture was extracted with ethyl acetate and post-treated to give (4R,5S)-cis-1,3-dibenzyl-5-n-propoxycarbonyl-2-oxoimidazolidine-4-carboxylic acid (0.22 g). M.P., 88°–92° C. $[\alpha]_{365}^{20} = +15.7°$ (c=0.35, DMF).

EXAMPLE 13

(1) A solution of (4S,5R)-1,3-dibenzyl-5-methoxycarbonyl-2-oxoimidazolidine-4-carboxylic acid (mp., 146°–150° C., $[\alpha]_{365}^{25} = -27.6°$ at c=1 in DMF, 3.68 g) in isopropanol (10 ml) and 1,2-dichloroethane (60 ml) was added dropwise to a mixture of sodium borohydride (760 mg) and isopropanol (20 ml) at 5°–10° C. over a period of 15 minutes. The obtained mixture was allowed to warm up to room temperature and to react at the same temperature for 20 hours. Then, 1N hydrochloric acid (50 ml) was added to the reaction mixture. The mixture was stirred at 55°–60° C. for 30 minutes. Aqueous layer was separated from organic layer and extracted once with 1,2-dichloroethane (50 ml). The organic layers were combined, washed successively with water, 5% aqueous sodium hydrogen carbonate, dried over anhydrous magnesium sulfate and concentrated under reduced pressure to give (3aS,6aR)-1,3-dibenzylhexahydro-1H-furo[3,4-d]imidazole-2,4-dione (3.12 g). M.P., 116°–117° C. $[\alpha]_D^{25} = +61.0°$ (c=1, CHCl$_3$).

(2) A solution of (4S,5R)-1,3-dibenzyl-5-methoxycarbonyl-2-oxoimidazolidine-4-carboxylic acid (mp., 149°–150° C., $[\alpha]_{365}^{25} = -27.6°$ at c=1 in DMF, 368 mg) in isopropanol (6 ml) was added dropwise to a mixture of sodium borohydride (98 mg) and isopropanol (8 ml) at 5°–10° C. The obtained mixture was allowed to warm up to room temperature for 20 hours. Then, 1N hydrochloric acid (10 ml) was added to the reaction mixture. The mixture was stirred at 55°–60° C. for 30 minutes and concentrated under reduced pressure. The residue was extracted with chloroform (30 ml) and water (30 ml). The chloroform layer was washed successively with 5% aqueous sodium hydrogen carbonate and water, dried over anhydrous magnesium sulfate and concentrated under reduced pressure. The residue was purified by chromatography on silica gel column to yield (3aS,6aR)-1,3-dibenzylhexahydro-1H-furo[3,4-d]imidazole-2,4-dione (82 mg). M.P., 116°–117° C. $[\alpha]_D^{25} = +61.2°$ (c=1, CHCl$_3$).

(3) A solution of (4S,5R)-1,3-dibenzyl-5-methoxycarbonyl-2-oxoimidazolidine-4-carboxylic acid (mp., 149°–150° C., $[\alpha]_{365}^{25} = -27.6°$ at c=1 in DMF, 368 mg) in tetrahydrofuran (6 ml) was added dropwise to a mixture of sodium borohydride (98 mg) and tetrahydrofuran (6 ml) at 5°–10° C. The obtained mixture was allowed to warm up to room temperature and to react at the same temperature for 20 hours. Then, 1N hydrochloric acid (10 ml) was added to the reaction mixture. The mixture was stirred at 55°–60° C. for 30 minutes and concentrated under reduced pressure. The residue was extracted with chloroform (30 ml) and water (30 ml). The chloroform layer was washed successively with 5% aqueous sodium hydrogen carbonate and water, dried over anhydrous magnesium sulfate and concentrated under reduced pressure. The residue was purified by chromatography on silica gel column to yield (3aS,6aR)-1,3-dibenzylhexahydro-1H-furo[3,4-d]imidazole-2,4-dione (45 mg). M.P., 116°–117° C. $[\alpha]_D^{25} = +60.9°$ (c=1, CHCl$_3$).

EXAMPLE 14

A solution of (4R,5S)-1,3-dibenzyl-5-methoxycarbonyl-2-oxoimidazolidine-4-carboxylic acid (mp., 149°–150° C., $[\alpha]_{365}^{25} = +27.7°$ at c=1.0 in DMF, 368 mg) in toluene (2 ml) and isopropanol (3 ml) was added dropwise to a suspension of sodium borohydride (100 mg) in toluene at 5°–10° C. The obtained mixture was allowed to warm up to room temperature and to react at the same temperature for 18 hours. Then, 1N hydrochloric acid (10 ml) was added dropwise to the mixture. The mixture was stirred at 55°–60° C. for 30 minutes. Aqueous layer was separated from organic layer and extracted once with toluene (15 ml). The organic layers were combined, washed successively with water, 5% aqueous sodium hydrogen carbonate and water, dried over anhydrous magnesium sulfate and concentrated to give (3aR,6aS)-1,3-dibenzylhexahydro-1H-furo[3,4-d]imidazole-2,4-dione (301 mg). M.P., 116°–118° C. $[\alpha]_D^{25} = -61.8°$ (c=1, CHCl$_3$).

EXAMPLE 15

A solution of (4S,5R)-1,3-dibenzyl-5-methoxycarbonyl-2-oxoimidazolidine-4-carboxylic acid (mp., 149°–150° C., $[\alpha]_{365}^{25} = -27.7°$ at c=1 in DMF, 368 mg) in tetrahydrofuran (3 ml) and isopropanol (0.50 g) was added dropwise to a mixture of sodium borohydride (100 mg) and tetrahydrofuran (3 ml) at 5°–10° C. The obtained mixture was allowed to warm up to room temperature and to react at the same temperature for 5 hours. Then, 1N hydrochloric acid (10 ml) was added dropwise to the reaction mixture. The mixture was stirred at 55°–60° C. for 30 minutes. Chloroform (30 ml) and water (30 ml) were added to the mixture. Aqueous layer was separated from organic layer and extracted once with chloroform. The organic layers were combined, washed successively with water, 5% aqueous sodium hydrogen carbonate and water, dried over anhydrous magnesium sulfate and concentrated under reduced pressure to give (3aS,6aR)-1,3-dibenzylhexahydro-1H-furo[3,4-d]imidazole-2,4-dione (314 mg). M.P., 116°–117° C. $[\alpha]_D^{25} = +61.1°$ (c=1, CHCl$_3$).

EXAMPLE 16

To a mixture of sodium borohydride (0.55 g) and 99.5% ethanol (20 ml) were added dropwise a solution of (4R,5S)-1,3-dibenzyl-5-methoxycarbonyl-2-oxoimidazolidine-4-carboxylic acid (mp., 149°–150° C., $[\alpha]_{365}^{25} = -27.7°$ at c=1 in DMF, 2.00 g) in 99.5% ethanol (30 ml) at 0°–5° C. and a solution of anhydrous calcium chloride (0.80 g) in 99.5% ethanol (8 ml) at the same temperature. The obtained mixture was allowed to warm up to room temperature and to react at the same temperature for 18 hours under stirring. Then, 1N hydrochloric acid was added dropwise to the reaction mixture. The solvent was removed from the mixture at 50°–55° C. under reduced pressure. The residue was shaken with chloroform (50 ml) and water (50 ml). Chloroform layer was washed successively with 5% aqueous sodium hydrogen carbonate and water, dried over anhydrous magnesium sulfate and concentrated under reduced pressure. The residue was treated with ether (10 ml), filtered and dried to give (3aS,6aR)-1,3-dibenzylhexahydro-1H-furo[3,4-d]imidazole-2,4-dione (1.43 g). M.P., 116°–117° C. $[\alpha]_D^{25} = +60.9°$ (c=1, CHCl$_3$).

EXAMPLE 17

To a solution of (4R,5S)-1,3-dibenzyl-5-methoxycarbonyl-2-oxoimidazolidine-4-carboxylic acid (mp., 149°–150° C., $[\alpha]_{365}^{25} = +27.4°$ at c=1 in DMF, 1.84 g) in tetrahydrofuran (15 ml) were added sodium borohydride (226 mg) in small portions at −20° C., and boron trifluoride etherate (1.06 g). The obtained mixture was stirred at the same temperature for 1 hour and at room temperature for 3 hours, poured into ice-water (50 ml), stirred further at room temperature, adjusted to pH 9 with aqueous potassium carbonate and extracted twice with ethyl acetate (50 ml). Organic layer was washed with saturated aqueous sodium chloride solution, dried over anhydrous magnesium sulfate and concentrated under reduced pressure. The residue was purified by chromatography on silica gel column to give (3aS,6aR)-1,3-dibenzylhexahydro-1H-furo[3,4-d]imidazole-2,4-dione (0.80 g). M.P., 114°–118° C. $[\alpha]_D^{20} = +59.8°$ (c=1, CHCl$_3$).

EXAMPLE 18

A solution of ethyl chloroformate (0.54 g) in tetrahydrofuran (2 ml) wasd added dropwise to a mixture of (4R,5S)-1,3-dibenzyl-5-methoxycarbonyl-2-oxoimidazolidine-4-carboxylic acid (mp., 149°–150° C., $[\alpha]_{365}^{25} = -27.4°$ at c=1 in DMF, 1.84 g), triethylamine (0.51 g) and tetrahydrofuran (10 ml) at −5° C. The mixture was stirred at the same temperature for 30 minutes. Precipitated triethylamine hydrochloride was filtered off and the filtrate was added dropwise to a solution of sodium borohydride (0.24 g) in 90% aqueous tetrahydrofuran (10 ml) at −15° C. After reacting, the mixture was acidified with diluted hydrochloric acid and extracted with ethyl acetate. The extract was concentrated under reduced pressure and the residue was purified by chromatography on silica gel column to give (3aS,6aR)-1,3-dibenzylhexahydro-1H-furo[3,4-d]imidazole-2,4-dione (1.04 g). M.P., 114°–117° C. $[\alpha]_D^{20} = +59.0°$ (c=1, CHCl$_3$).

EXAMPLE 19

To a suspension of (4R,5S)-1,3-dibenzyl-5-methoxycarboxyl-2-oxoimidazolidine-4-carboxylic acid (mp., 149°–150° C., $[\alpha]_{365}^{25} = +27.7°$ at c=1 in DMF, 3.68 g) in benzene (40 ml), there was dropwise added thionyl chloride (2.38 g) at room temperature. The obtained mixture was refluxed for 2 hours and concentrated under reduced pressure. The residue was dissolved in tetrahydrofuran (20 ml) and added dropwise to a suspension of sodium borohydride (0.76 g) in tetrahydrofuran (10 ml) at 0°–5° C. The mixture was stirred at the same temperature for 3 hours. To this mixture was added dropwise 1N hydrochloric acid (20 ml). The reaction mixture was stirred further at 50°–55° C. for 30 minutes. The solvent was removed from the mixture under reduced pressure. The residue was extracted with chloroform (100 ml) and water (100 ml). Chloroform layer was washed successively with 5% aqueous sodium hydrogen carbonate and water, dried over anhydrous magnesium sulfate and concentrated under reduced pressure. The residue was purified by chromatography on silica gel column to give (3aS,6aR)-1,3-dibenzylhexahydro-1H-furo[3,4-d]imidazole-2,4-dione (0.97 g). M.P., 114°–116° C. $[\alpha]_D^{25} = +58.5°$ (c=1, CHCl$_3$).

What is claimed is:

1. A process for preparing an optically active cis-imidazolidinedicarboxylic acid monoester of the formula:

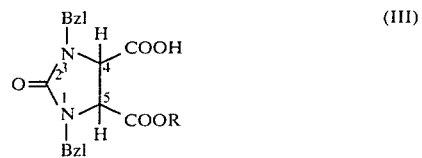

(III)

wherein R is a C$_1$–C$_6$ alkyl group, Bzl represents a benzyl group and the 4- and 5-positions take the 4S,5R-configuration, which comprises hydrolyzing a cis-imidazolidinedicarboxylic acid diester of the formula:

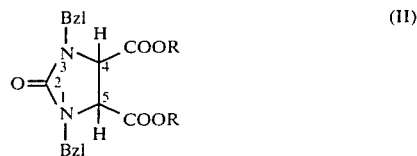

(II)

wherein R and Bzl are each as defined above with an enzymatic material having a capability of hydrolyzing the ester group in the said diester.

2. The process according to claim 1, wherein the enzymatic material is an esterase originating from pig liver.

3. The process according to claim 1, wherein the enzymatic material is an esterase originating from a microorganism belonging to Genus Chromobacterium.

4. The process according to claim 3, wherein the microorganism is *Chromobacterium chocolatum*.

5. The process according to claim 1, wherein the enzymatic material is a microorganism belonging to Genus Chromobacterium.

6. The process according to claim 5, wherein the microorganism is *Chromobacterium chocolatum*.

7. The process according to claim 1, wherein the hydrolysis is carried out in an aqueous medium having a pH of 5 to 9 at a temperature of 10° to 40° C.

8. A process for preparing an optically active cis-1,3-dibenzylhexahydro-1H-furo[3,4-d]imidazole-2,4-dione of the formula:

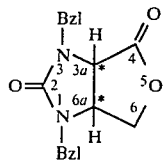

wherein an asterisk (*) indicates an asymmetric carbon, Bzl represents a benzyl group and the 3a- and 6a-positions take the cis-configuration, which comprises reducing selectively an optically active cis-imidazolidinedicarboxylic acid monoester of the formula:

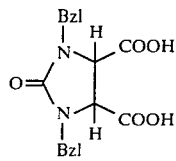

wherein R is a $C_1$–$C_6$ alkyl group and Bzl is as defined above with a reducing agent prepared from sodium borohydride and boron trifluoride for selective reduction of the carboxyl group or with sodium borohydride, in a mixture of at least one alcoholic solvent and at least one aprotic solvent, as the reducing agent for selective reduction of the alkoxycarbonyl group, followed by cyclization.

9. The process according to claim 8, wherein the reduction is carried out using diborane as the reducing agent for selective reduction of the carboxyl group.

10. The process according to claim 9, wherein diborane is the one prepared from sodium borohydride and boron trifluoride.

11. The process according to claim 8, wherein the reduction is carried out using sodium borohydride as the reducing agent for selective reduction of the alkoxycarbonyl group.

12. The process according to claim 11, wherein the reduction is carried out in a mixture of at least one alcoholic solvent and at least one aprotic solvent.

13. The process according to claim 8, wherein the starting monoester has the 4S,5R-configuration, the selective reduction proceeds at the alkoxycarbonyl group and the produced lactone has the 3aS,6aR-configuration.

14. The process according to claim 8, wherein the starting monoester has the 4S,5R-configuration, the selective reduction proceeds at the carboxyl group and the produced lactone has the 3aR,6aS-configuration.

15. The process according to claim 8, wherein the starting monoester has the 4R,5S-configuration, the selective reduction proceeds at the carboxyl group and the produced lactone has the 3aS,6aR-configuration.

16. The process according to claim 8, wherein the starting monoester has the 4R,5S-configuration, the selective reduction proceeds at the alkoxycarbonyl group and the produced lactone has the 3aR,6aS-configuration.

17. The process according to claim 8, wherein the starting monoester is the one prepared by hydrolyzing a cis-imidazolidinedicarboxylic acid diester of the formula:

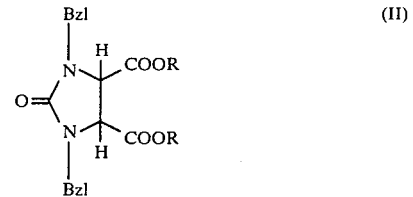

wherein R is a $C_1$–$C_6$ alkyl group and Bzl represents a benzyl group with an enzymatic material having a capability of hydrolyzing the ester group in the said diester.

* * * * *

UNITED STATES PATENT AND TRADEMARK OFFICE
CERTIFICATE OF CORRECTION

PATENT NO. : 4,544,635
DATED : October 1, 1985
INVENTOR(S) : Naohito OHASHI et al It is certified that error appears in the above-identified patent and that said Letters Patent is hereby corrected as shown below:

IN THE HEADING OF THE PATENT:

In the Abstract, change:

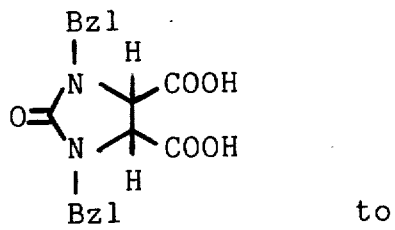

to

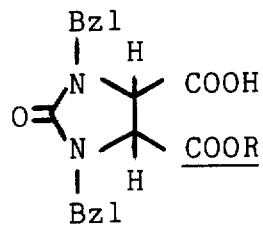

UNITED STATES PATENT AND TRADEMARK OFFICE
CERTIFICATE OF CORRECTION

PATENT NO. : 4,544,635

DATED : October 1, 1985

INVENTOR(S) : Naohito Ohashi et al

It is certified that error appears in the above-identified patent and that said Letters Patent is hereby corrected as shown below:

IN THE BODY OF THE PATENT:

In the Column 17, change:

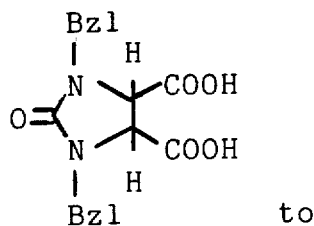  to

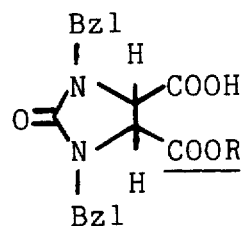

Signed and Sealed this

First Day of July 1986

[SEAL]

Attest:

DONALD J. QUIGG

Attesting Officer    Commissioner of Patents and Trademarks